United States Patent
Thakur (10) Patent No.: US 11,179,055 B2
(45) Date of Patent: Nov. 23, 2021

(54) CALIBRATING INTRATHORACIC IMPEDANCE FOR ABSOLUTE LUNG FLUID MEASUREMENT

(71) Applicant: Cardiac Pacemakers, Inc., St. Paul, MN (US)

(72) Inventor: Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1599 days.

(21) Appl. No.: 14/875,960

(22) Filed: Oct. 6, 2015

(65) Prior Publication Data

US 2016/0095534 A1    Apr. 7, 2016

Related U.S. Application Data

(60) Provisional application No. 62/060,883, filed on Oct. 7, 2014.

(51) Int. Cl.
*A61B 5/0537* (2021.01)
*A61B 5/0536* (2021.01)
(Continued)

(52) U.S. Cl.
CPC .......... *A61B 5/0537* (2013.01); *A61B 5/0536* (2013.01); *A61B 5/0809* (2013.01);
(Continued)

(58) Field of Classification Search
CPC .... A61B 5/0537; A61B 5/0536; A61B 5/0809
See application file for complete search history.

(56) References Cited

U.S. PATENT DOCUMENTS 7,794,404 B1   9/2010  Gutfinger et al.
8,099,146 B1   1/2012  Koh
(Continued)

FOREIGN PATENT DOCUMENTS

CN    103370004 A    10/2013
CN    106793951 A     5/2017
(Continued)

OTHER PUBLICATIONS

Amir, Offer, et al., "A Novel Approach to Monitoring Pulmonary Congestion in Heart Failure: Initial Animal and Clinical Experiences Using Remote Dielectric Sensing Technology", Congest Heart Fail. 2013; 19, (2013), 149-155.
(Continued)

*Primary Examiner* — Daniel L Cerioni
*Assistant Examiner* — Yasmeen S Warsi
(74) *Attorney, Agent, or Firm* — Schwegman Lundberg & Woessner, P.A.

(57) ABSTRACT

In one example, a method of estimating lung fluid content includes receiving a first response signal in response to a delivered first test stimulus, the first test stimulus delivered and the first response signal obtained during a first subject state, receiving a first estimate of a fluid content value during the first subject state, receiving a second response signal in response to a delivered second test stimulus, the second test stimulus delivered and the second response signal obtained during a second subject state, receiving a second estimate of the fluid content value during the second subject state, pairing the first response signal and the first estimate of the fluid content value to form a first pair of values and pairing the second response signal and the second estimate of the fluid content value to form a second pair of values, and determining a relationship between the pairs of values.

19 Claims, 4 Drawing Sheets

(51) Int. Cl.
*A61B 5/08* (2006.01)
*A61B 5/00* (2006.01)

(52) U.S. Cl.
CPC .......... *A61B 5/4842* (2013.01); *A61B 5/4878* (2013.01); *A61B 5/686* (2013.01); *A61B 5/7282* (2013.01); *A61B 5/0004* (2013.01); *A61B 5/0031* (2013.01)

(56) References Cited

U.S. PATENT DOCUMENTS

| | | |
|---|---|---|
| 2006/0064029 A1 | 3/2006 | Arad (Abboud) |
| 2010/0056907 A1 | 3/2010 | Rappaport et al. |
| 2010/0256462 A1 | 10/2010 | Rappaport et al. |
| 2010/0305643 A1 | 12/2010 | Emerson |
| 2011/0025295 A1 | 2/2011 | Saroka et al. |
| 2011/0160549 A1 | 6/2011 | Saroka et al. |
| 2011/0319746 A1 | 12/2011 | Kochba et al. |
| 2012/0035495 A1 | 2/2012 | Gutfinger et al. |
| 2012/0190991 A1 | 7/2012 | Bornzin et al. |
| 2013/0060103 A1 | 3/2013 | Bergida et al. |
| 2013/0116583 A1 | 5/2013 | Min |
| 2013/0184545 A1 | 7/2013 | Blomqvist |
| 2013/0281800 A1 | 10/2013 | Saroka et al. |
| 2013/0317378 A1 | 11/2013 | Krivitski et al. |
| 2014/0276166 A1 | 9/2014 | Drori et al. |

FOREIGN PATENT DOCUMENTS

| | | |
|---|---|---|
| WO | WO-2012103576 A1 | 8/2012 |
| WO | WO-2016057461 A1 | 4/2016 |

OTHER PUBLICATIONS

"European Application Serial No. 15790318.8, Response filed Nov. 17, 2017 to Communication Pursuant to Rules 161(1) and 162 EPC dated May 16, 2017", 19 pgs.
"International Application Serial No. PCT/US2015/054148, International Preliminary Report on Patentability dated Apr. 20, 2017", 8 pgs.
"International Application Serial No. PCT/US2015/054148, International Search Report dated Jan. 8, 2016", 6 pgs.
"International Application Serial No. PCT/US2015/054148, Written Opinion dated Jan. 8, 2016", 28 pgs.
Belalcazar, Andres, et al., "Improved lung edema monitoring with coronary vein pacing leads: a simulation study", Physiological Measurement, vol. 25, No. 2, (Apr. 1, 2004), 475-487.
Urooj, Shabana, et al., "Prediction of quantitative intrathoracic fluid volume to diagnose pulmonary oedema using LabVIEW", Computer Methods in Biomechanics and Biomedical??Engineering, vol. 15, No. 8,, (Aug. 1, 2012), 859-865.
"Chinese Application Serial No. 201580054245.5, Office Action dated Mar. 27, 2019", w/ English summary, 12 pgs.
"Chinese Application Serial No. 201580054245.5, Decision of Rejection dated Nov. 17, 2020", w/ English Translation, 19 pgs.
"Chinese Application Serial No. 201580054245.5, Office Action dated Feb. 7, 2020", w/English Translation, 13 pgs.
"Chinese Application Serial No. 201580054245.5, Office Action dated Jun. 10, 2020", With English Translation, 21 pgs.
"Chinese Application Serial No. 201580054245.5, Response filed Apr. 22, 20 to Office Action dated Feb. 7, 2020", w/ English Claims, 31 pgs.
"Chinese Application Serial No. 201580054245.5, Response filed Aug. 21, 20 to Office Action dated Jun. 10, 2020", w/ current English claims, 12 pgs.
"European Application Serial No. 15790318.8, Communication Pursuant to Article 94(3) EPC dated Apr. 24, 2020", 7 pgs.

CALIBRATING INTRATHORACIC IMPEDANCE FOR ABSOLUTE LUNG FLUID MEASUREMENT

CLAIM OF PRIORITY

This application claims the benefit of priority under 35 U.S.C. § 119(e) of U.S. Provisional Patent Application Ser. No. 62/060,883, titled "CALIBRATING INTRATHORACIC IMPEDANCE FOR ABSOLUTE LUNG FLUID MEASUREMENT" to Pramodsingh H. Thakur and filed on Oct. 7, 2014, which is herein incorporated by reference in its entirety.

TECHNICAL FIELD

This document pertains generally, but not by way of limitation, to techniques for monitoring pulmonary congestion.

BACKGROUND

One hallmark of chronic heart failure (CHF) in a subject is congestion, more commonly referred to as fluid retention. Reasons for fluid retention are complex and multifactoral. Fluid retention or accumulation in the lungs or other respiratory organs (e.g., the trachea, the bronchi, etc.) is referred to as Pulmonary Edema (PE). In certain examples, fluid can accumulate in extracellular spaces, such as the spaces between lung tissue cells, commonly referred to as interstitial pulmonary edema. If left untreated, fluid can move from the extracellular space into the lung air-sacs, commonly referred to as alveolar pulmonary edema. One of the most common systems of heart failure is shortness of breath resulting from pulmonary congestion.

Another example of thoracic fluid accumulation is pleural effusion, which is the buildup of extravascular fluid in the space between the lungs and the rib cage. Pleural effusion can also result from CHF because, as discussed above, intravascular fluid buildup can result in the extravascular interstitial fluid buildup. The extravascular fluid buildup of pulmonary edema can, in turn, result in the extravascular fluid buildup of pleural effusion.

Fluid accumulation in the thorax corresponds to a decrease in the thoracic impedance. Conversely, fluid depletion in the thorax corresponds to an increase in the thoracic impedance. Thus, intrathoracic impedance values can be used to monitor fluid accumulation, or pulmonary congestion.

Intrathoracic impedance values, however, can vary between patients and within a patient over time. For example, the specific geometry of the electrode placement can vary between patients, resulting in different impedance values. As another example, chest cavity size and tissue composition can vary between patients, each of which can affect impedance values. Within a patient, changes in tissue composition, e.g., hematocrit changes, fat content, can also affect impedance values over time. Thus, clinicians are reluctant to rely on absolute impedance values in determining fluid accumulation. Instead, clinicians may observe impedance values for each patient over time in a relative sense.

U.S. Pat. No. 7,794,404 to Gutfinger et al. discloses that left atrial pressure (LAP) is effective in detecting CHF and describes techniques to provide estimates of LAP to a physician, rather than raw impedance signal values. For example, U.S. Pat. No. 7,794,404 describes detecting conductance and LAP calibration readings and calculating a slope value, which can be used to estimate LAP.

OVERVIEW

In general, this disclosure describes, among other things, techniques for estimating a fluid content value of a tissue of interest, e.g., lung fluid value, based upon a measured intrathoracic impedance value using a relationship between previously measured intrathoracic impedance and lung fluid values. These techniques can allow a clinician to monitor a fluid content value directly, rather than monitoring a proxy value, such as an impedance signal value.

In one example, this disclosure is directed a machine-implemented method of estimating lung fluid content using an intrathoracic impedance measurement. The method comprise receiving a first intrathoracic electrical response signal from a tissue of interest in a subject in response to a delivered first subcapture electrical test stimulus, the first test stimulus delivered and the first response signal obtained during a first subject state. The method comprises receiving a first estimate of a fluid content value of the tissue of interest during the first subject state. The method comprises receiving a second intrathoracic electrical response signal from the tissue of interest in the subject in response to a delivered second subcapture electrical test stimulus, the second test stimulus delivered and the second response signal obtained during a second subject state. The method comprises receiving a second estimate of the fluid content value of the tissue of interest during the second subject state. The method comprises pairing the first intrathoracic electrical response signal and the first estimate of the fluid content value to form a first pair of values and pairing the second intrathoracic electrical response signal and the second estimate of the fluid content value to form a second pair of values. The method comprises determining a relationship between the first and second pairs of values.

In another example, this disclosure is directed to a system comprising one or more physiological signal processor circuits configured to receive a first intrathoracic electrical response signal from a tissue of interest in a subject in response to a delivered first subcapture electrical test stimulus, the first test stimulus delivered and the first response signal obtained during a first subject state, receive a first estimate of a fluid content value of the tissue of interest during the first subject state, receive a second intrathoracic electrical response signal from the tissue of interest in the subject in response to a delivered second subcapture electrical test stimulus, the second test stimulus delivered and the second response signal obtained during a second subject state, receive a second estimate of the fluid content value of the tissue of interest during the second subject state, pair the first intrathoracic electrical response signal and the first estimate of the fluid content value to form a first pair of values and pair the second intrathoracic electrical response signal and the second estimate of the fluid content value to form a second pair of values, and determine a relationship between the first and second pairs of values.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
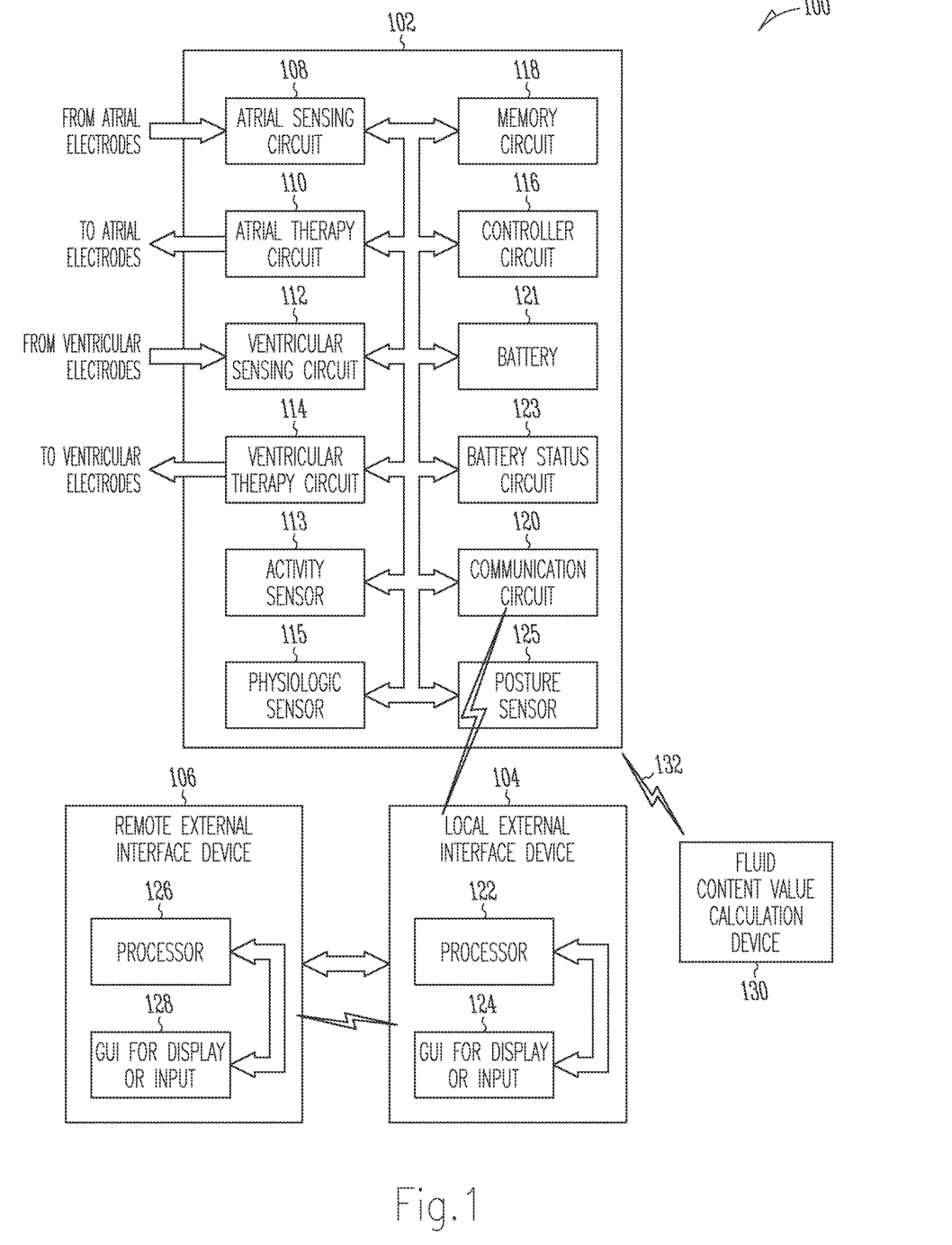
FIG. 1 is a block diagram depicting an example of a system including an implantable medical device that can implement various techniques of this disclosure.

FIG. 1 show an example of portions of a system 100 that can be used to implement various techniques of this disclosure. The system 100 can include an implantable medical device (IMD) 102 (e.g., a pacemaker, cardiac resynchronization management device, defibrillator, etc.), a local external interface device 104, and a remote external interface device 106.

The implantable device 102 can optionally include one or more of an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, a battery status circuit 123, an activity sensor 113 configured to sense a physical activity signal of a patient or other subject, a physiologic sensor 115 configured to sense a physiologic signal (e.g., different from the physical activity signal of the subject), and a posture sensor 125.

The atrial sensing circuit 108 can include one or more channels and can be coupled to electrodes, such as an intra-atrial electrode or any other electrode that permits sensing of an intrinsic atrial cardiac signal including atrial depolarization information. The atrial therapy circuit 110 can include one or more channels and can similarly be coupled to these or other electrodes, such as for delivering pacing, cardiac resynchronization therapy (CRT), cardiac contractility modulation (CCM) therapy, defibrillation/cardioversion shocks, or other energy pulses to one or both atria.

The ventricular sensing circuit 112 can include one or more channels and can be coupled to electrodes, such as an intra-ventricular electrode, an LV/CS electrode, or any other electrode that permits sensing of an intrinsic ventricular cardiac signal including ventricular depolarization information. The ventricular therapy circuit 114 can include one or more channels and can similarly be coupled to these or other electrodes, such as for delivering pacing, cardiac resynchronization therapy (CRT), cardiac contractility modulation (CCM) therapy, defibrillation/cardioversion shocks, or other energy pulses to one or both ventricles.

The activity sensor 113 can include a single or multiple axis accelerometer, such as to sense an acceleration of the subject that is indicative of physical activity of the subject. The activity sensor 113 can also include a sensor interface circuit, configured to process the acceleration signal and provide a resulting physical activity signal. The physical activity signal can be indicative of a physical exertion of the subject. The activity sensor 113 can also be used for other purposes, such as to sense the subject's posture, heart sounds, or other information available from an acceleration signal. A separate posture sensor 125 can optionally be provided, such as a tilt-switch, a separate single or multiple axis accelerometer, or other sensor capable of providing a posture-indicative signal, either directly or extracted from other physiologic information, which can be sensed by the posture sensor 125 or obtained from the physiologic sensor 115.

The physiologic sensor 115 can include an impedance (or other physiological conductivity characteristic) sensor, a respiration sensor, or another sensor. In an example, the physiologic sensor 115 can include a respiration sensor that can sense respiration via a physiologic impedance (or other physiological conductivity characteristic) signal that can be provided by an impedance or other sensor. The impedance or other physiological conductivity sensor can include or be coupled to electrodes configured to deliver a test energy, such as a subcapture test energy delivered to the subject's thorax, and to sense a responsive voltage signal, such as indicative of the thoracic impedance or thoracic conductivity. The resulting thoracic impedance or conductivity signal can be filtered to provide information about respiration, heart contraction, or thoracic fluid accumulation.

The electrodes used for impedance monitoring can include one or any combination of one or more right atrial (RA) electrodes, one or more right ventricular (RV) electrodes, one or more LV/CS electrodes such as can be located on a bipolar or quadripolar LV/CS lead, one or more wired or wireless epicardial electrodes, IMD electronics unit housing or header electrodes, or one or more other implantable or wearable electrodes. The impedance monitoring is merely an example of monitoring a physiological conductivity characteristic, other examples of which can include voltage monitoring, transimpedance monitoring, transconductance monitoring, etc.

In various examples, the physiologic sensor 115 can be configured to provide information about heart rate, heart rate variability, autonomic balance, heart vibrations, intracardiac pressure, thoracic fluid status, respiration, patient activity level, temperature, pH, potassium levels, oxygenation, cardiac volumes, blood pressure, or ejection fraction.

A physiological signal processor circuit 116 (also referred to in this disclosure as "controller circuit 116") can be coupled to the atrial sensing circuit 108 and the ventricular sensing circuit 112, such as to receive information from the sensed cardiac signals. The controller circuit 116 can also be coupled to the activity sensor 113 to receive information about the subject's physical activity or exertion level. The controller circuit 116 can also be coupled to the physiologic sensor 115, such as to receive other physiologic information. The other physiologic information can include a cardiac contraction signal, such as to provide information about the subject's heart rate or interval, stroke volume, or other information available from the cardiac contraction signal. In an example, the other physiologic information can include a respiration signal, such as to provide information about the subject's breathing rate or interval, tidal volume, or other information available from the respiration signal.

The controller circuit 116 can include a signal processor circuit, e.g., a digital signal processor (DSP) circuit, for extracting a parameter from which a diagnostic indicator can be generated, as described below. The signal processor circuit can include dedicated circuitry for performing one or more signal processing functions. The controller circuit 116 can be coupled to the atrial therapy circuit 110 and the ventricular therapy circuit 114 to provide control or triggering signals, such as to trigger timed delivery of the therapy pulses. The controller circuit 116 can be configured to provide control to help permit therapy to be effectively delivered, such as in combination with one or more other therapies (e.g., bradycardia pacing, antitachy arrhythmia pacing (ATP), cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.) In an example, this can include providing dedicated modules within the controller circuit 116, or providing executable, interpretable, or otherwise performable code to configure the controller circuit 116.

A memory circuit 118 can be included in or coupled to the controller circuit 116, such as to store control parameter values, physiological data, or other information. A communication circuit 120 can be coupled to the controller circuit 116, such as to permit radiofrequency (RF) or other wireless communication with an external device, such as the local external interface device 104 or the remote external interface device 106.

The battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

The local external interface device 104 can include a processor circuit 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 can include a processor circuit 126 and a graphic user interface (GUI) 128 or like device for displaying information or receiving user input as well as a communication circuit, such as to permit wired or wireless communication with the local external interface device 104 over the communications or computer network.

Because the system 100 includes processing capability in the ambulatory or implantable device 102 (e.g., provided by the controller circuit 116), the local external interface device 104 (e.g., provided by the physiological signal processor circuit 122), and the remote external interface device 106 (e.g., provided by the physiological signal processor circuit 126), various techniques discussed in this document can be implemented at any of such locations, or tasks can be distributed between two or more of such locations.

In accordance with this disclosure, one or more components of the system 100 in FIG. 1 can be configured to estimate a fluid content value of a tissue of interest (e.g., a lung fluid value, such as a percentage), based upon a measured intrathoracic impedance value using a relationship between previously measured intrathoracic impedance and fluid content values of the tissue of interest. For example, during a first subject state, the physiological signal processor circuit 116 of FIG. 1 can be configured to control delivery of a first subcapture electrical test stimulus through one or more electrodes to a tissue of interest, e.g., lung tissue. The physiological signal processor circuit 116 can receive the resulting first intrathoracic electrical response signal, e.g., impedance signal.

In one example, the first subject state can include a first posture, e.g., upright, and a second subject state can include a second posture, e.g., recumbent. The posture state can be detected by posture sensor 125, for example. In another example, the first subject state can include a first medication state, e.g., prior to receiving a diuretic medication, and a second subject state can include a second medication state, e.g., after receiving a diuretic medication. In another example, the first subject state can include a first liquid state, e.g., prior to receiving an intravenous bolus of saline or other intravenous fluid, and a second subject state can include a second liquid state, e.g., after receiving an intravenous bolus of saline.

The one or more electrodes used to deliver the electrical test stimulus can include, for example, one or any combination of one or more right atrial (RA) electrodes, one or more right ventricular (RV) electrodes, one or more LV/CS electrodes such as can be located on a bipolar, tripolar, quadripolar, or any other multipolar LV/CS lead, one or more wired or wireless epicardial electrodes, IMD electronics unit housing or header electrodes, or one or more other implantable or wearable electrodes. The impedance sensor 115 can include or be coupled to the one or more electrodes configured to deliver a test energy.

While the subject is in the first subject state, e.g., an upright posture state, a first estimate of a fluid content value of the tissue of interest, e.g., absolute lung fluid value, can be estimated using a fluid content value calculation device 130. In some examples, the fluid content value calculation device 130 can use an electromagnetic radiation procedure to estimate an absolute lung fluid value.

In one example of an electromagnetic radiation procedure, a remote dielectric sensing (ReDS) technique can be used to estimate a fluid content value of the tissue of interest, e.g., an absolute lung fluid value. Generally speaking and without being bound by theory, wearable sensors on either side of a subject's chest can intercept delivered electromagnetic waves focused on a tissue of interest, e.g., lung tissue, which are indicative of a dielectric property of the tissue. The dielectric property of the tissue, e.g., dielectric coefficient, is directly related to the fluid content of the tissue. The dielectric coefficient of the tissue can increase as the fluid content increases. Example remote dielectric sensing techniques for estimating absolute lung fluid are described in detail in U.S. patent application Ser. No. 12/676,381 to Rappaport et al., titled "METHOD AND SYSTEM FOR MONITORING THORACIC TISSUE FLUID" and assigned to Sensible Medical Innovations Ltd., the content of which is incorporated by reference herein in its entirety.

In another example of an electromagnetic radiation procedure, an x-ray tomography procedure, e.g., computed tomography (CT), can be used to estimate a fluid content value of the tissue of interest, e.g., an absolute lung fluid value. For example, a CT image is a 3-dimensional image that can include a plurality of voxels. An absolute lung fluid value can be estimated using the CT image by determining how many voxels are wet and how many are dry and calculating a percentage, for example.

In one example implementation, after the first fluid content value of the tissue of interest, e.g., absolute lung fluid value, is estimated by the fluid content value calculation device 130, one or more of the physiological signal processor circuits of FIG. 1 can be used to pair the first fluid content value of the tissue of interest with the first intrathoracic impedance signal value to form a first pair of values. For example, in one implementation, the physiological signal processor circuit 116 of the IMD 102 can control the communication circuit 120 to transmit the first intrathoracic impedance signal value to the local external interface device 104. The local external interface device 104 can receive the first intrathoracic impedance signal value and the first absolute lung fluid value (e.g., transmitted from the lung fluid value calculation device 130 via a communication link 132) and, in response, the physiological signal processor circuit 122 of the local external interface device 104 can associate, e.g., pair, the first absolute lung fluid value and the first intrathoracic impedance signal value to form a first pair of values.

In another example implementation, the physiological signal processor circuit 116 of the IMD 102 can control the communication circuit 120 to receive the first absolute lung fluid value (e.g., transmitted from the fluid content value calculation device 130 via a communication link 132). In response, the physiological signal processor circuit 116 of the IMD 102 can associate, e.g., pair, the first absolute lung fluid value and the first intrathoracic impedance signal value to form a first pair of values.

In another example implementation, the physiological signal processor circuit 126 of the remote external interface device can associate, e.g., pair, the first absolute lung fluid value and the first intrathoracic impedance signal value to form a first pair of values. In such an implementation, the IMD 102 and the lung fluid value calculation device 130 can transmit the first intrathoracic impedance signal value and the first absolute lung fluid value, respectively, to the remote external interface device, e.g., via the local interface device 104.

Next, during a second subject state, e.g., a recumbent posture state, the physiological signal processor circuit 116 of FIG. 1 can be configured to control delivery of a second subcapture electrical test stimulus through one or more electrodes to a tissue of interest. The physiological signal processor circuit 116 can receive the resulting second intrathoracic electrical response signal, e.g., impedance signal.

While the subject is in the second subject state, e.g., a recumbent posture state, a second fluid content value of the tissue of interest, e g, absolute lung fluid value, can be estimated using the fluid content value calculation device 130, as described above. After the second fluid content value, e.g., absolute lung fluid value, is estimated by the fluid content value calculation device 130, one or more of the physiological signal processor circuits of FIG. 1 can be used to pair the second fluid content value of the tissue of interest with the second intrathoracic impedance signal value to form a second pair of values. Various example implementations were described above with respect to pairing the values and, for purposes of conciseness, will not be described in detail again.

It should be noted that the techniques of this disclosure are not limited to any particular order. For example, the first tissue fluid content value can be determined before, after, or at the same time at which the first intrathoracic impedance signal value is determined. Similarly, the second tissue fluid content value can be determined before, after, or at the same time at which the second intrathoracic impedance signal value is determined. In addition, the second tissue fluid content value and the second intrathoracic impedance signal value can be determined prior to pairing the first tissue fluid content value with the first intrathoracic impedance signal value. That is, each of the first and second tissue fluid content value and the first and second intrathoracic impedance signal values can be determined and then paired to form first and second pairs of values.

After pairing the first and second values, one or more of the physiological signal processor circuits of FIG. 1 can be used to determining a relationship between the first and second pairs of values, as described below with respect to FIG. 2.

Figure 2:
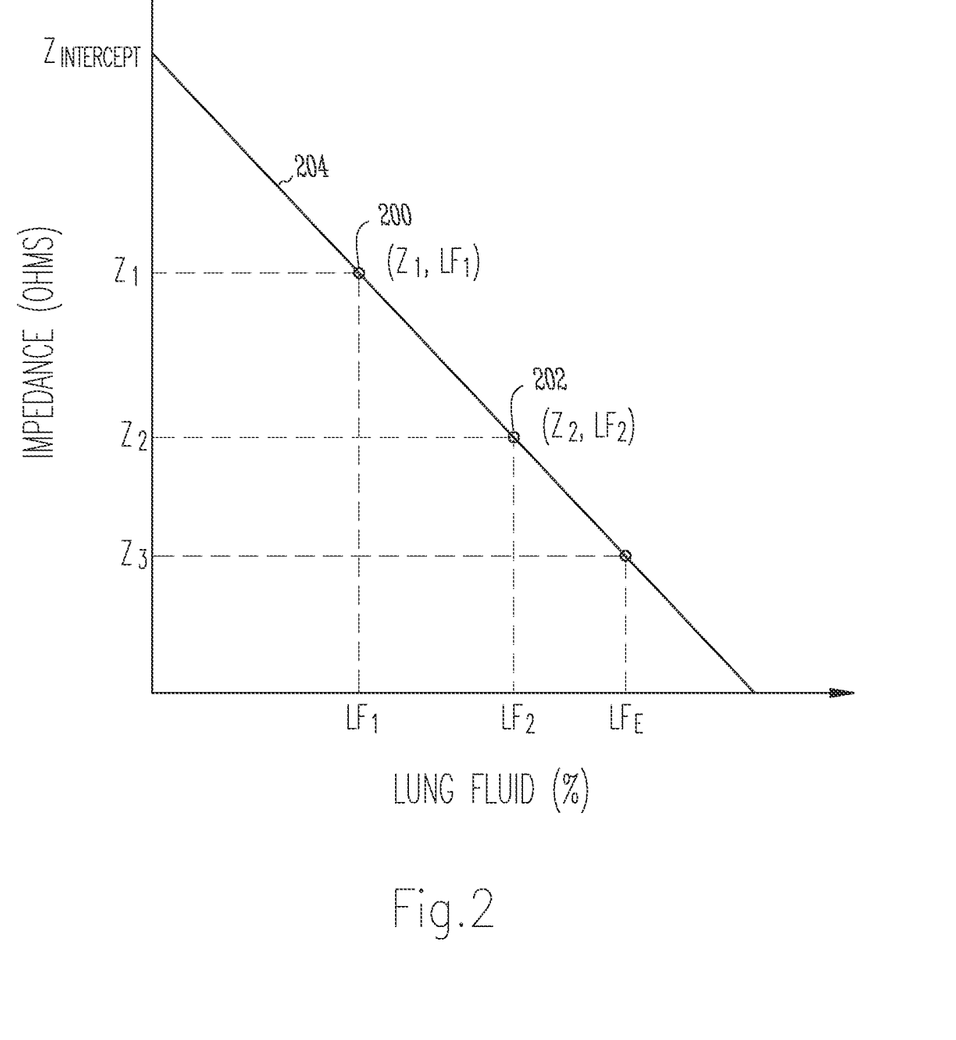
FIG. 2 is a graph depicting an example of a relationship between first and second pairs of values, in accordance with various techniques of this disclosure.

FIG. 2 is a graph depicting an example of a relationship between first and second pairs of tissue fluid content and intrathoracic impedance signal values, in accordance with various techniques of this disclosure. In the graph of FIG. 2, the x-axis represents an absolute lung fluid value, e.g., percentage, and the y-axis represents an intrathoracic impedance signal value, e.g., ohms.

The first intrathoracic impedance signal value ("$Z_1$") and the first lung fluid value ("$LF_1$"), which were determined in the manner described above, are shown as a first pair of values 200. The second intrathoracic impedance signal value ("$Z_2$") and the second lung fluid value ("$LF_2$"), are shown as a second pair of values 202. One or more of the physiological signal processor circuits of FIG. 1 can be used to determine a relationship between the first and second pairs of values 200, 202. For example, as shown in FIG. 2, one or more of the physiological signal processor circuits of FIG. 1 can determine a linear relationship between the first and second pairs of values 200, 202, where the linear relationship is defined by a line 204 having a slope and a y-intercept at an impedance of $Z_{intercept}$.

In accordance with this disclosure, one or more of the physiological signal processor circuits of FIG. 1 can determine a third estimate of the fluid content value of the tissue of interest, e.g., lung fluid, based upon a received third intrathoracic electrical response signal obtained from the tissue of interest in the subject in response to a delivered third subcapture electrical test stimulus and using the determined relationship between the first and second pairs of values. For example, the physiological signal processor circuit 116 of FIG. 1 can be configured to control delivery of a third subcapture electrical test stimulus through one or more electrodes to the tissue of interest, e.g., lung tissue. The physiological signal processor circuit 116 can receive the resulting third intrathoracic electrical response signal, e.g., impedance signal. Using the determined relationship between the first and second pairs of values, e.g., the slope and y-intercept of a linear fit relationship, the physiological signal processor circuit 116 (or one or both of the processor circuits 122, 126) can determine a third estimate of the fluid content value of the tissue of interest, e.g., lung fluid.

This technique is graphical depicted in FIG. 2. The physiological signal processor circuit 116 can receive the resulting third intrathoracic electrical response signal value, e.g., impedance signal value "$Z_3$." Using the determined relationship between the first and second pairs of values 200, 202 defined by the line 204, the physiological signal processor circuit 116 (or one or both of the processor circuits 122, 126) can determine, e.g., interpolate, an estimate of the fluid content value of the tissue of interest, e.g., lung fluid value estimate "$LF_E$". Then, one or more of the physiological signal processor circuits of FIG. 1 can transmit the determined lung value estimate $LF_E$ for display to a clinician, for example. In this manner and in accordance with this disclosure, the clinician can directly evaluate an estimated tissue fluid content value, e.g., lung fluid value, of a patient to determine a progression of CHF, instead of evaluating a measured impedance value, which can vary between patients and within patient.

It should be noted that although the techniques above describe using two pairs of values from which a relationship is determined, in some example implementations, three or more pairs of values can be used for determining a relationship. In such example implementations, one or more of the physiological signal processor circuits of FIG. 1 can determine a linear fit relationship, a curvilinear fit relationship, or some other relationship between the three or more pairs of values, from which an estimate of fluid content value can be determined, e.g., interpolated.

Figure 3:
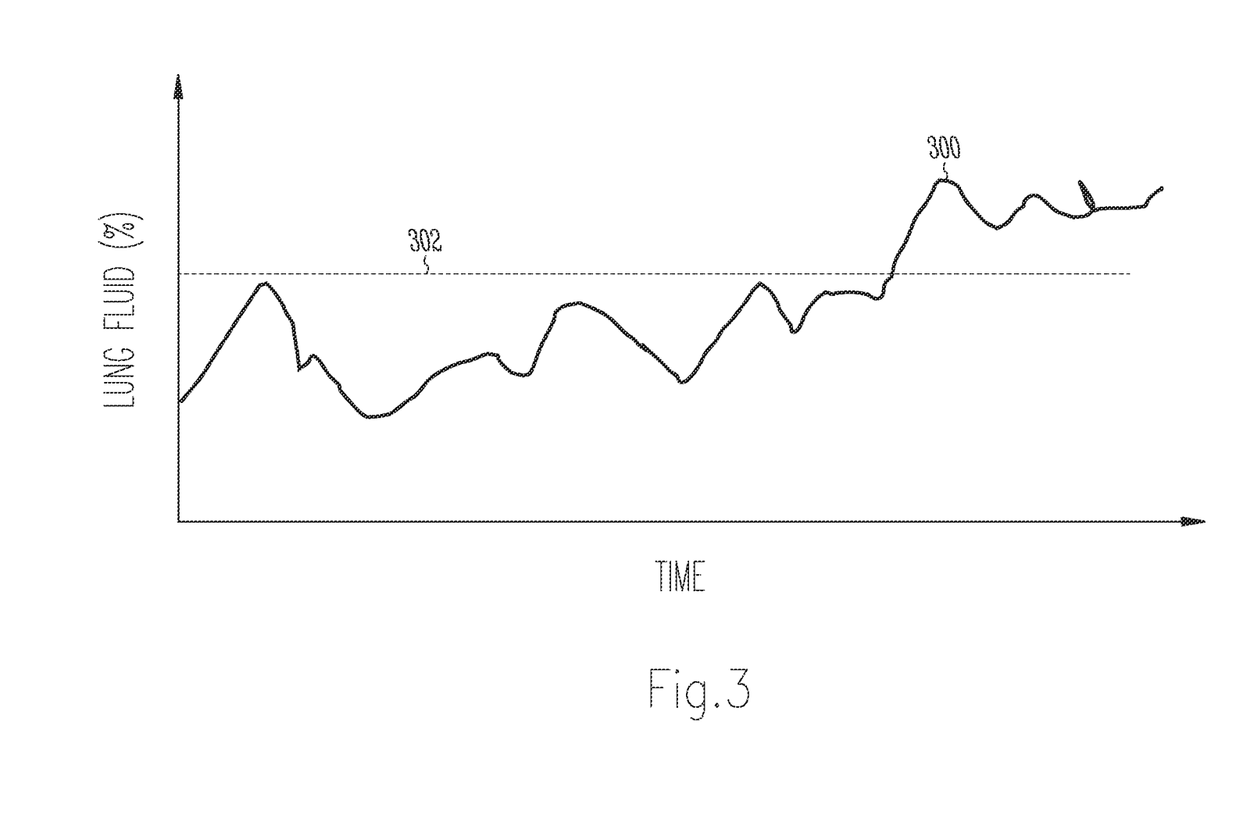
FIG. 3 is a conceptual diagram depicting monitoring an impedance-based lung fluid percentage with respect to a criterion, in accordance with various techniques of this disclosure.

FIG. 3 is a conceptual diagram depicting monitoring an impedance-based lung fluid percentage with respect to a criterion, in accordance with various techniques of this disclosure. The y-axis in FIG. 2 represents a lung fluid percentage and the x-axis represents time, e.g., in days, weeks, etc.

Using various techniques of this disclosure, an impedance-based lung fluid estimate at 300 can be monitored over time and compared to a criterion, e.g., a specified threshold, a change, or a rate of change. For example, a plurality of lung fluid value estimates, e.g., a plurality of "$LF_E$" values of FIG. 2, can be determined over time (shown at 300) and compared to a lung fluid threshold 302, as seen in FIG. 3. If a lung fluid value estimate 300 meets a specified criterion 302, one or more of the physiological signal processor circuits of FIG. 1 can generate an alert. The alert can provide to a subject and/or a clinician an indication that the subject should be seen by a clinician, e.g., for treatment.

Figure 4:
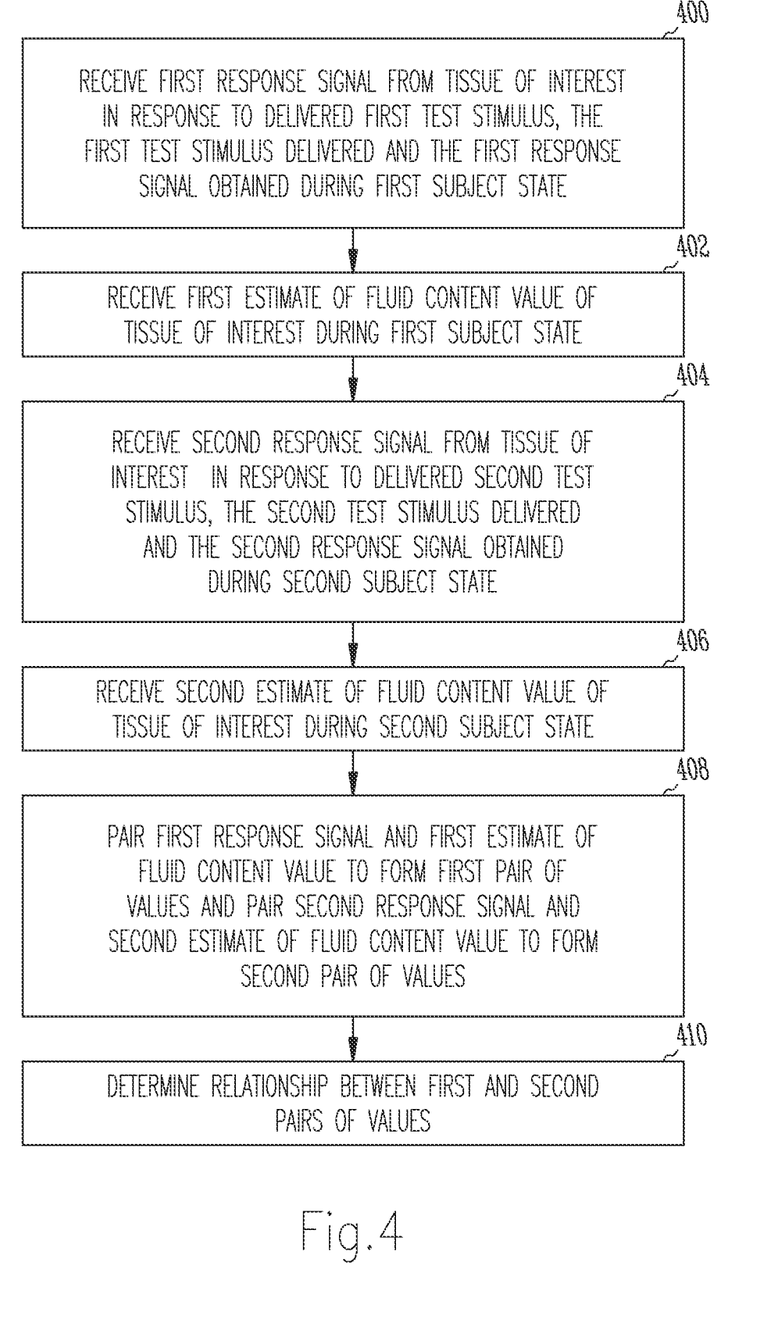
FIG. 4 is a flowchart depicting an example of a technique for estimating a lung fluid percentage, in accordance with various techniques of this disclosure.

FIG. 4 is a flowchart depicting an example of a technique for estimating a lung fluid percentage, in accordance with various techniques of this disclosure. In FIG. 4, one or more of the physiological signal processor circuits of FIG. 1 can receive a first intrathoracic electrical response signal, e.g., an impedance signal value, from a tissue of interest in a subject, e.g., lung tissue, in response to a delivered first subcapture electrical test stimulus, wherein the first test stimulus is delivered and the first response signal is obtained during a first subject state, e.g., a first posture state (block 400). One or more of the physiological signal processor circuits of FIG. 1 can receive a first estimate of a fluid content value of the tissue of interest during the first subject state (block 402).

One or more of the physiological signal processor circuits of FIG. 1 can receive a second intrathoracic electrical response signal, e.g., an impedance signal value, from a tissue of interest in a subject, e.g., lung tissue, in response to a delivered second subcapture electrical test stimulus, where the second test stimulus is delivered and the second response signal is obtained during a second subject state, e.g., a second posture state (block 404). One or more of the physiological signal processor circuits of FIG. 1 can receive a second estimate of a fluid content value of the tissue of interest during the second subject state (block 406).

One or more of the physiological signal processor circuits of FIG. 1 can pair the first intrathoracic electrical response signal and the first estimate of the fluid content value to form a first pair of values and pair the second intrathoracic electrical response signal and the second estimate of the fluid content value to form a second pair of values (block 408). Then, one or more of the physiological signal processor circuits of FIG. 1 can determine a relationship between the first and second pairs of values (block 410).

Optionally, and in addition to the techniques described above, this disclosure includes techniques for determining a calibration recurrence frequency based on a last clinician visit calibration and a current clinician visit calibration. For example, an amount of calibration drift can be estimated and, based on the estimated drift, a calibration recurrence frequency can be determined. The calibration recurrence frequency can indicate when the subject should have the determined relationship between measured pairs of values recalibrated, e.g., measure two new pairs of values and determine a new relationship using those two new pairs of values.

In one example implementation of a calibration recurrence frequency determination technique, the physiological signal processor circuit 116 of FIG. 1 can control delivery of a third subcapture electrical test stimulus and one or more of the physiological signal processor circuits of FIG. 1 can determine a third estimate of the fluid content value of the tissue of interest based upon a received third intrathoracic electrical response signal obtained from the tissue of interest in the subject in response to the delivered third subcapture electrical test stimulus and the determined relationship between the first and second paired values, e.g., determine an "$LF_E$" value as shown in FIG. 2. One or more of the physiological signal processor circuits of FIG. 1 can receive a fourth estimate of a fluid content value of the tissue of interest obtained during a first subject state using an electromagnetic radiation procedure, e.g., in a manner similar to that used to determine "$LF_1$" in FIG. 2.

Then, one or more of the physiological signal processor circuits of FIG. 1 can determine a difference between the third estimate and the fourth estimate, e.g., an estimate of the drift, and determine a calibration recurrence frequency based on the determined difference. For example, if a drift of less than 5% over a 3 month period was desirable, but a 10% drift was determined over a 3 month period, then one or more of the physiological signal processor circuits of FIG. 1 can determine a calibration recurrence frequency to be less than the 3 month period, e.g., 1.5 months. In this manner, measurement drift can be countered by more frequent calibrations.

It should be noted that although the techniques above were described with respect to an implantable medical device, e.g., implantable device 102 of FIG. 1, this disclosure is not so limited. Rather, various techniques of this disclosure can also be performed using a subcutaneous diagnostic device.

Additional Notes and Examples

Example 1 includes subject matter (such as a system or apparatus) comprising: one or more physiological signal processor circuits configured to: receive a first intrathoracic electrical response signal from a tissue of interest in a subject in response to a delivered first subcapture electrical test stimulus, the first test stimulus delivered and the first response signal obtained during a first subject state; receive a first estimate of a fluid content value of the tissue of interest during the first subject state; receive a second intrathoracic electrical response signal from the tissue of interest in the subject in response to a delivered second subcapture electrical test stimulus, the second test stimulus delivered and the second response signal obtained during a second subject state; receive a second estimate of the fluid content value of the tissue of interest during the second subject state; pair the first intrathoracic electrical response signal and the first estimate of the fluid content value to form a first pair of values and pair the second intrathoracic electrical response signal and the second estimate of the fluid content value to form a second pair of values; and determine a relationship between the first and second pairs of values.

In Example 2, the subject matter of Example 1 optionally includes wherein the one or more physiological signal processor circuits are configured to: determine a third estimate of the fluid content value of the tissue of interest based upon a received third intrathoracic electrical response signal obtained from the tissue of interest in the subject in response to a delivered third subcapture electrical test stimulus during a first subject state and using the determined relationship between the first and second pairs of values.

In Example 3, the subject matter of one or more combinations of Examples 1 and 2 optionally includes wherein the one or more physiological signal processor circuits are configured to: generate an alert if the third estimate meets a specified criterion.

In Example 4, the subject matter of one or more combinations of Examples 1-3 optionally includes wherein to receive a first estimate of a fluid content value of the tissue of interest obtained during the first subject state, the one or more physiological signal processor circuits are configured to receive a first estimate of a fluid content value of the tissue of interest obtained during the first subject state using an electromagnetic radiation procedure, and wherein to receive a second estimate of the fluid content value of the tissue of interest obtained during the second subject state, the one or more physiological signal processor circuits are configured to receive a second estimate of the fluid content value of the tissue of interest obtained during the second subject state using the electromagnetic radiation procedure.

In Example 5, the subject matter of one or more combinations of Examples 1-4 optionally includes wherein to receive a first estimate of a fluid content value of the tissue of interest obtained during the first subject state using an electromagnetic radiation procedure, the one or more physiological signal processor circuits are configured to receive at least one parameter indicative of a first dielectric coefficient of the tissue of interest, wherein to receive a second estimate of the fluid content value of the tissue of interest obtained during the second subject state using the electromagnetic radiation procedure, the one or more physiological signal processor circuits are configured to receive at least one parameter indicative of a second dielectric coefficient of the tissue of interest, and wherein the first and second dielectric coefficients are indicative of the fluid content of the tissue of interest.

In Example 6, the subject matter of one or more combinations of Examples 1-5 optionally includes wherein the electromagnetic radiation procedure includes a tomography procedure.

In Example 7, the subject matter of one or more combinations of Examples 1-6 optionally includes wherein the first subject state is a first posture, and wherein the second subject state is a second posture.

In Example 8, the subject matter of one or more combinations of Examples 1-7 optionally includes wherein the first subject state is a first medication state, and wherein the second subject state is a second medication state.

In Example 9, the subject matter of one or more combinations of Examples 1-8 optionally includes wherein the first subject state is prior to receiving a bolus of saline, and wherein the second subject state is after receiving the bolus of saline.

In Example 10, the subject matter of one or more combinations of Examples 1-9 optionally includes wherein the one or more physiological signal processor circuits are configured to: determine a third estimate of the fluid content value of the tissue of interest based upon a received third intrathoracic electrical response signal obtained from the tissue of interest in the subject in response to a delivered third subcapture electrical test stimulus and using the determined relationship between the first and second pairs of values; receive a fourth estimate of a fluid content value of the tissue of interest obtained during the first subject state; determine a difference between the third estimate and the fourth estimate; and determine a calibration recurrence frequency based on the determined difference.

Example 11 can include subject matter (such as a method, a means for performing acts, or a machine-readable medium including instructions that, when performed by the machine, cause the machine to perform acts), or can optionally be combined with the subject matter of one or any combination of Examples 1-10 to include such subject matter, comprising: receiving a first intrathoracic electrical response signal from a tissue of interest in a subject in response to a delivered first subcapture electrical test stimulus, the first test stimulus delivered and the first response signal obtained during a first subject state; receiving a first estimate of a fluid content value of the tissue of interest during the first subject state; receiving a second intrathoracic electrical response signal from the tissue of interest in the subject in response to a delivered second subcapture electrical test stimulus, the second test stimulus delivered and the second response signal obtained during a second subject state; receiving a second estimate of the fluid content value of the tissue of interest during the second subject state; pairing the first intrathoracic electrical response signal and the first estimate of the fluid content value to form a first pair of values and pairing the second intrathoracic electrical response signal and the second estimate of the fluid content value to form a second pair of values; and determining a relationship between the first and second pairs of values.

In Example 12, the subject matter of Example 11 optionally includes determining a third estimate of the fluid content value of the tissue of interest based upon a received third intrathoracic electrical response signal obtained from the tissue of interest in the subject in response to a delivered third subcapture electrical test stimulus during a first subject state and using the determined relationship between the first and second pairs of values.

In Example 13, the subject matter of one or more combinations of Examples 11-12 optionally includes generating an alert if the third estimate meets a specified criterion.

In Example 14, the subject matter of one or more combinations of Examples 11-13 optionally includes wherein receiving a first estimate of a fluid content value of the tissue of interest obtained during the first subject state includes receiving a first estimate of a fluid content value of the tissue of interest obtained during the first subject state using an electromagnetic radiation procedure, and wherein receiving a second estimate of the fluid content value of the tissue of interest obtained during the second subject state includes receiving a second estimate of the fluid content value of the tissue of interest obtained during the second subject state using the electromagnetic radiation procedure.

In Example 15, the subject matter of one or more combinations of Examples 11-14 optionally includes wherein receiving a first estimate of a fluid content value of the tissue of interest obtained during the first subject state using an electromagnetic radiation procedure includes receiving at least one parameter indicative of a first dielectric coefficient of the tissue of interest, wherein receiving a second estimate of the fluid content value of the tissue of interest obtained during the second subject state using the electromagnetic radiation procedure includes receiving at least one parameter indicative of a second dielectric coefficient of the tissue of interest, and wherein the first and second dielectric coefficients are indicative of the fluid content of the tissue of interest.

In Example 16, the subject matter of one or more combinations of Examples 11-15 optionally includes wherein the electromagnetic radiation procedure includes a tomography procedure.

In Example 17, the subject matter of one or more combinations of Examples 11-16 optionally includes wherein the first subject state is a first posture, and wherein the second subject state is a second posture.

In Example 18, the subject matter of one or more combinations of Examples 11-17 optionally includes wherein the first subject state is a first medication state, and wherein the second subject state is a second medication state.

In Example 19, the subject matter of one or more combinations of Examples 11-18 optionally includes wherein the first subject state is prior to receiving a bolus of saline, and wherein the second subject state is after receiving the bolus of saline.

In Example 20, the subject matter of one or more combinations of Examples 11-19 optionally includes determining a third estimate of the fluid content value of the tissue of interest based upon a received third intrathoracic electrical response signal obtained from the tissue of interest in the subject in response to a delivered third subcapture electrical test stimulus and using the determined relationship between the first and second pairs of values; receiving a fourth estimate of a fluid content value of the tissue of interest obtained during the first subject state; determining a difference between the third estimate and the fourth estimate; and determining a calibration recurrence frequency based on the determined difference.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A machine-implemented method comprising:
calibrating an absolute intrathoracic electrical response signal of a first medical device using an estimate of a fluid content value from a fluid content value calculation device separate from the first medical device, comprising:
receiving a first absolute intrathoracic electrical response signal from a tissue of interest in a subject in response to a delivered first subcapture electrical test stimulus, the first test stimulus delivered and the first response signal obtained during a first subject state from the first medical device;
receiving a first estimate of a fluid content value of the tissue of interest during the first subject state from the fluid content value calculation device separate from the first medical device;
receiving a second absolute intrathoracic electrical response signal from the tissue of interest in the subject in response to a delivered second subcapture electrical test stimulus, the second test stimulus delivered and the second response signal obtained during a second subject state from the first medical device;

receiving a second estimate of the fluid content value of the tissue of interest during the second subject state from the fluid content value calculation device;

pairing the first absolute intrathoracic electrical response signal and the first estimate of the fluid content value to form a first pair of values and pairing the second absolute intrathoracic electrical response signal and the second estimate of the fluid content value to form a second pair of values;

determining a relationship between the first and second pairs of values; and calibrating the first absolute intrathoracic electrical response signal, the second absolute intrathoracic response signal, or a received third absolute intrathoracic electrical response signal from the tissue of interest in the subject using the determined relationship.

2. The method of claim 1, comprising:
determining a third estimate of the fluid content value of the tissue of interest based upon the received third intrathoracic electrical response signal obtained from the tissue of interest in the subject in response to a delivered third subcapture electrical test stimulus during a first subject state and using the determined relationship between the first and second pairs of values.

3. The method of claim 1,
wherein receiving a first estimate of a fluid content value of the tissue of interest obtained during the first subject state includes receiving a first estimate of a fluid content value of the tissue of interest obtained during the first subject state using an electromagnetic radiation procedure, and wherein receiving a second estimate of the fluid content value of the tissue of interest obtained during the second subject state includes receiving a second estimate of the fluid content value of the tissue of interest obtained during the second subject state using the electromagnetic radiation procedure.

4. The method of claim 1,
wherein the first subject state is a first posture, and
wherein the second subject state is a second posture different than the first posture.

5. The method of claim 1,
wherein the first subject state is a first medication state, and
wherein the second subject state is a second medication state.

6. The method of claim 1,
wherein the first subject state is prior to receiving a bolus of saline, and
wherein the second subject state is after receiving the bolus of saline.

7. The method of claim 1, comprising:
determining a third estimate of the fluid content value of the tissue of interest based upon the received third intrathoracic electrical response signal obtained from the tissue of interest in the subject in response to a delivered third subcapture electrical test stimulus and using the determined relationship between the first and second pairs of values;
receiving a fourth estimate of a fluid content value of the tissue of interest obtained during the first subject state;
determining a difference between the third estimate and the fourth estimate; and
determining a calibration recurrence frequency based on and adaptive to the determined difference.

8. A system comprising:
one or more physiological signal processor circuits configured to calibrate an absolute intrathoracic electrical response signal of a first medical device using an estimate of a fluid content value from a fluid content value calculation device separate from the first medical device, wherein, to calibrate the absolute intrathoracic electrical response signal, the one or more physiological signal processor circuits are configured to:
receive a first intrathoracic electrical response signal from a tissue of interest in a subject in response to a delivered first subcapture electrical test stimulus, the first test stimulus delivered and the first response signal obtained during a first subject state from the first medical device;

receive a first estimate of a fluid content value of the tissue of interest during the first subject state from the fluid content value calculation device separate from the first medical device;

receive a second intrathoracic electrical response signal from the tissue of interest in the subject in response to a delivered second subcapture electrical test stimulus, the second test stimulus delivered and the second response signal obtained during a second subject state from the first medical device;

receive a second estimate of the fluid content value of the tissue of interest during the second subject state from the fluid content value calculation device;

pair the first intrathoracic electrical response signal and the first estimate of the fluid content value to form a first pair of values and pair the second intrathoracic electrical response signal and the second estimate of the fluid content value to form a second pair of values;

determine a relationship between the first and second pairs of values; and calibrate the first intrathoracic electrical response signal, the second intrathoracic response signal, or a received third intrathoracic electrical response signal from the tissue of interest in the subject using the determined relationship.

9. The system of claim 8, wherein the one or more physiological signal processor circuits are configured to:
determine a third estimate of the fluid content value of the tissue of interest based upon the received third intrathoracic electrical response signal obtained from the tissue of interest in the subject in response to a delivered third subcapture electrical test stimulus during a first subject state and using the determined relationship between the first and second pairs of values.

10. The system of claim 8,
wherein to receive a first estimate of a fluid content value of the tissue of interest obtained during the first subject state, the one or more physiological signal processor circuits are configured to receive a first estimate of a fluid content value of the tissue of interest obtained during the first subject state using an electromagnetic radiation procedure, and wherein to receive a second estimate of the fluid content value of the tissue of interest obtained during the second subject state, the one or more physiological signal processor circuits are configured to receive a second estimate of the fluid content value of the tissue of interest obtained during the second subject state using the electromagnetic radiation procedure.

11. The system of claim 10, wherein to receive a first estimate of a fluid content value of the tissue of interest obtained during the first subject state using an electromagnetic radiation procedure, the one or more physiological signal processor circuits are configured to receive at least one parameter indicative of a first dielectric coefficient of the tissue of interest, wherein to receive a second estimate of the fluid content value of the tissue of interest obtained during the second subject state using the electromagnetic radiation procedure, the one or more physiological signal processor circuits are configured to receive at least one parameter indicative of a second dielectric coefficient of the tissue of interest, and wherein the first and second dielectric coefficients are indicative of the fluid content of the tissue of interest.

12. The system of claim 8, wherein the first subject state is a first posture, and wherein the second subject state is a second posture different than the first posture.

13. The system of claim 8, wherein the first subject state is a first medication state, and wherein the second subject state is a second medication state.

14. The system of claim 8, wherein the first subject state is prior to receiving a bolus of saline, and wherein the second subject state is after receiving the bolus of saline.

15. The system of claim 8, wherein the one or more physiological signal processor circuits are configured to:

determine a third estimate of the fluid content value of the tissue of interest based upon the received third intrathoracic electrical response signal obtained from the tissue of interest in the subject in response to a delivered third subcapture electrical test stimulus and using the determined relationship between the first and second pairs of values;

receive a fourth estimate of a fluid content value of the tissue of interest obtained during the first subject state;

determine a difference between the third estimate and the fourth estimate; and determine a calibration recurrence frequency based on and adaptive to the determined difference.

16. The system of claim 8, wherein the fluid content value calculation device includes a wearable device coupled to the first medical device using a communication link.

17. The system of claim 16, wherein the first medical device includes an implantable medical device.

18. The method of claim 1, wherein the fluid content value calculation device includes a wearable device coupled to the first medical device using a communication link.

19. The method of claim 18, wherein the first medical device includes an implantable medical device.

* * * * *